US007766478B2

(12) United States Patent
Phillips (10) Patent No.: US 7,766,478 B2
(45) Date of Patent: Aug. 3, 2010

(54) CONTACT LENS AND METHOD FOR PREVENTION OF MYOPIA PROGRESSION

(75) Inventor: John R. Phillips, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 508 days.

(21) Appl. No.: 11/631,124

(22) PCT Filed: Jul. 1, 2005

(86) PCT No.: PCT/NZ2005/000155

§ 371 (c)(1),
(2), (4) Date: Apr. 24, 2007

(87) PCT Pub. No.: WO2006/004440

PCT Pub. Date: Jan. 12, 2006

(65) Prior Publication Data

US 2008/0062380 A1     Mar. 13, 2008

Related U.S. Application Data

(60) Provisional application No. 60/584,894, filed on Jul. 1, 2004.

(51) Int. Cl.
*G02B 15/14* (2006.01)
(52) U.S. Cl. ...................... 351/161; 351/177
(58) Field of Classification Search ............ 351/160 R, 351/160 H, 161, 177, 221
See application file for complete search history.

(56) References Cited

U.S. PATENT DOCUMENTS

| 4,618,228 A | 10/1986 | Baron et al. |
| 4,704,016 A | 11/1987 | De Carle |
| 4,890,913 A | 1/1990 | De Carle |
| 5,002,382 A | 3/1991 | Seidner |
| 5,024,517 A | 6/1991 | Seidner |
| 5,349,393 A | 9/1994 | Kreft |
| 5,448,312 A | 9/1995 | Roffman et al. |
| 5,485,228 A | 1/1996 | Roffman et al. |
| 5,898,473 A | 4/1999 | Seidner et al. |

(Continued)

FOREIGN PATENT DOCUMENTS

EP     0 742 463 A2     11/1996

(Continued)

OTHER PUBLICATIONS

Notification Concerning Transmittal of International Preliminary Report on Patentability; International Appln. No. PCT/NZ2005/000155, International Filing Date Jul. 1, 2005.

(Continued)

*Primary Examiner*—Scott J Sugarman
(74) *Attorney, Agent, or Firm*—Nixon & Vanderhye (57) ABSTRACT

A method of slowing the progression of myopia in a person, comprises applying to the eye of the person contact lens or lenses each including a vision correction area for correcting in use the myopic vision of a wearer, and a myopic defocus area having a less negative focal power, to simultaneously present a controlled myopic defocus to the retina both when viewing in the distance and also when viewing at near. Contact lenses and their use are also claimed.

19 Claims, 4 Drawing Sheets

DISTANCE VISION

NEAR VISION
(crystalline lens accommodated)

U.S. PATENT DOCUMENTS

| | | | |
|---|---|---|---|
| 5,929,969 | A | 7/1999 | Roffman |
| 6,045,578 | A | 4/2000 | Collins et al. |
| 6,752,499 | B2 | 6/2004 | Aller |
| 7,025,460 | B2 * | 4/2006 | Smitth et al. ............... 351/221 |
| 7,401,922 | B2 | 7/2008 | Legerton |
| 2001/0033363 | A1 | 10/2001 | Chateau et al. |
| 2003/0058404 | A1 | 3/2003 | Thorn et al. |
| 2003/0058407 | A1 | 3/2003 | Aller |
| 2004/0237971 | A1 * | 12/2004 | Radhakrishnan et al. .... 128/898 |
| 2005/0099597 | A1 | 5/2005 | Sandstedt et al. |
| 2006/0082729 | A1 | 4/2006 | To et al. |
| 2006/0232743 | A1 | 10/2006 | Legerton |
| 2008/0291393 | A1 | 11/2008 | Menezes |

FOREIGN PATENT DOCUMENTS

| | | |
|---|---|---|
| EP | 0 742 464 A2 | 11/1996 |
| WO | WO 99/66366 | 12/1999 |
| WO | WO 2004/068214 A1 | 8/2004 |
| WO | WO 2004/113959 A2 | 12/2004 |
| WO | WO 2006/034652 A1 | 4/2006 |
| WO | WO 2009/129528 A1 | 10/2009 |

OTHER PUBLICATIONS

Zhu, X., et al; "Potency of Myopic Defocus in Spectacle Lens Compensation"; *Investigative Ophthalmology of Visual Science*; vol. 44, No. 7, pp. 2818-2827 (2003).

Chung, K., et al; "Undercorrection of myopia enhances rather than inhibits myopia progression"; *Vision Research*; vol. 42; pp. 2555-2559 (2002).

Wallman, J., et al; "Might myopic defocus prevent myopia?"; *Proceedings of the Eighth International Conference on Myopia*; pp. 138-142, (2000).

Choo, J.D., et al; "The Prevention of Myopia with Contact Lenses"; *Eye & Contact Lens*; vol. 33, No. 6; pp. 371-372 (2007).

Khoo, et al; "Methodologies for Interventional Myopia Studies"; *Annals Academy of Medicine*; vol. 35, No. 4, pp. 282-286 (2006).

Saw, S.M., et al; "Is it Possible to Slow the Progression of Myopia?"; *Annals of Academy of Medicine*; vol. 33, No. 1; pp. 4-6 (2004).

Saw, S.M., et al; "Myopia: attempts to arrest progression"; *Br. J. Ophthalmol.*; vol. 86, pp. 1306-1311 (2002).

Smith III, E.L., et al; "Peripheral Vision Can Influence Eye Growth and Refractive Development in Infant Monkeys"; *Investigative Ophthalmology & Visual Science*; vol. 46, No. 11; pp. 3965-3972 (2005).

Smith III, E.L., et al; "The role of optical defocus in regulating refractive development in infant monkeys"; *Vision Research*; vol. 39, pp. 1415-1435 (1999).

Aller, T.A., et al; "Results of a one-year prospective clinical trial (Control) of the use of bifocal soft contact lenses to control myopia progression"; *Ophthal, Physiol, Opt.* 26 (Suppl 1): 1-67 (2006).

\* cited by examiner

CONTACT LENS AND METHOD FOR PREVENTION OF MYOPIA PROGRESSION

This application is the U.S. National Phase of International Application PCT/NZ2005/000155, filed 1 Jul. 2005, which designated the U.S. PCT/NZ2005/000155 claims priority from U.S. provisional Application No. 60/584,894 filed 1 Jul. 2004. The entire content of these applications are incorporated herein by reference.

FIELD OF INVENTION

The invention relates to a contact lens and method for prevention of myopia progression.

BACKGROUND

Myopia (also called sort-sight) is a common ocular condition in which distant objects appear blurred whereas near objects are seen clearly. The prevalence of myopia, which is about 25% in developed countries and may be 70-80% in parts of Asia, has significant socioeconomic and public health consequences. Even people with relatively low degrees of myopia usually require an optical correction (eg spectacles or contact lenses) to allow them to drive a car or see the school blackboard, whereas those with high myopia also have an increased risk of developing blinding conditions such as retinal detachment and glaucoma. Myopia often develops during childhood and typically increases in severity (requiring progressively stronger spectacles to correct it) until early adulthood, although the final amount of myopia that develops will vary between individuals.

Myopia is generally characterised by an abnormal enlargement of the eye-ball which has the effect of moving the light-sensitive tissue (the retina in the back of the eye) out of the focal plane of the optical components of the eye. Thus, images of distant objects are brought to focus in front of the retina, rather than in the plane of the retina. Images of distant objects are therefore seen as blurred. In high levels of myopia, the marked enlargement of the eye-ball also results in a stretching of the retina and its associated blood supply, which renders the eye more susceptible to retinal detachment, glaucomatous damage and degenerative myopic retinopathy.

The aetiology of myopia is poorly understood. Both genetic and environmental factors have been implicated and in susceptible individuals myopia progression is thought to be associated with excessive near work (eg reading), possibly because the prolonged muscular effort of focussing the eyes at near (accommodation) results in a lag of accommodation (insufficient accommodation) and hyperopic retinal defocus. The correction of myopia requires minus-powered lenses which demand a greater accommodative effort for near work than is required without the lenses. This greater effort (and thus greater accommodative lag) has been implicated in exacerbating myopia progression and attempts have been made to reduce it by prescribing bifocal spectacles or Progressive Addition Lenses (PALs). Most evidence indicates that if bifocals/PALs slow myopia progression compared to conventional lenses, then it is only by a small amount. A variety of other methods have been used in attempts to slow myopia progression (eg vision therapy, distance under-correction and biofeedback training) but there is no convincing evidence that myopia progression is reduced by these procedures. In one recent study (Chung, Mohidin & O'Leary, Undercorrection of myopia enhances rather than inhibits myopia progression, Vision Research, 42 (2002) 2555-2559) 47 children had their myopia undercorrected by 0.75 D (which reduced their distance vision to 6/12). Over a period of two years, the progression of myopia in these children was shown to be significantly greater than in a control group of children wearing a full conventional correction. They concluded that myopic defocus speeds up myopia development in already myopic children. However, although bilateral under-correction results in myopic retinal defocus for distance viewing, clear retinal images in both eyes are experienced for near viewing. Use of pharmacological agents, in particular atropine eye-drops, to reduce myopia progression has been investigated in several studies and recent trials have provided evidence that repeated instillation of atropine may be effective in reducing myopia progression. However, myopia typically progresses over a number of years. The prospect of applying drug therapies long-term to large numbers of healthy children poses significant problems in relation to drug toxicity and other unwanted side effects.

Animal studies have demonstrated that the normal developing eye grows in a coordinated manner so that the length of the eye matches the power of its optical components, resulting in emmetropia (no refractive error). Furthermore, when a lens is placed in front of a developing animal's eye, the eye alters its growth in such a way as to compensate for the imposed defocus. Over time, the eye adjusts its axial dimensions to achieve functional emmetropia with the lens in place. Thus, eyes that have worn minus lenses (initially causing hyperopic retinal defocus, with images focused behind the retina) become elongated and are thus myopic on lens removal. Eyes that have worn plus lenses (causing myopic retinal defocus, with images focussed in front of the retina) are shortened and are thus hyperopic (long sighted) on lens removal. Such compensatory responses to defocusing lenses have been demonstrated in several species, ranging from chick to monkey.

SUMMARY OF INVENTION

In broad terms in one aspect the invention comprises a contact lens including a vision correction area for correcting in use the myopic vision of a wearer, and a myopic defocus area for simultaneously in use presenting a myopic defocused image to the wearer at all levels of accommodation.

In broad terms in another aspect of the invention comprises a method of treating or slowing the progression of myopia in a person, which includes applying to the eye(s) of the person or prescribing for the person, a contact lens or lens(es) each including a vision correction area for correcting in use the myopic vision of a wearer, and a myopic defocus area which simultaneously in use presents a myopic defocused image to the wearer.

The contact lens and method of the invention are aimed at slowing myopia progression in humans, in particular in children and young adults. The lens is intended to correct preexisting myopia (allowing the wearer to see distant objects clearly, as a normal contact lens), while also including a myopic defocus area or 'treatment zone' which applies a controlled myopic defocus to the retina both when the wearer is viewing in the distance and also when viewing at near, in order to slow the progression of myopia. A focussed retinal image and a myopic defocused retinal image during both distance and near viewing are simultaneously presented to the eye(s) of the wearer.

This invention provides a new means and method for treating myopia progression in people with myopia with contact lenses which both correct their myopic refractive error and simultaneously provide an optical treatment to slow the progression of myopia. The optical treatment consists of continuous myopic retinal defocus which is created by the contact lenses both during distance viewing and also during near viewing.

The invention also includes use, in the manufacture of a contact lens system or kit for treating or slowing the progression of myopia in a patient, of two or more contact lenses which may be the same or different, at least one of which includes a vision correction area for correcting in use the myopic vision of the patient and a myopic defocus area for simultaneously presenting in use a myopic defocused image to the patient.

The invention also includes a method of correcting myopic vision while causing lens-induced functional emmetropia in a person, which includes applying to at least one of the person's eyes a contact lens including a vision correction area for correcting in use the myopic vision of the person and a myopic defocus area for simultaneously presenting in use a myopic defocused image to the person.

The invention also includes use of a contact lens including a vision correction area for correcting in use the myopic vision of a person and a myopic defocus area for simultaneously presenting in use a myopic defocused image to the person, for the technical purpose of correcting the person's myopic vision causing lens-induced functional emmetropia on application of the contact lens to the person's eye.

BRIEF DESCRIPTION OF THE FIGURES

The invention is further described with reference to the accompanying Figures, by way of example and without intending to be limiting, in which:

FIGS. 6a and 6b are data for 13 myopic children.

FIGS. 7a and 7b show that the changes in myopia progression resulting from sustained myopic defocus are well explained by the changes in eye growth brought about by the myopic defocus. The slopes of these relationships (−2.16 D/mm to −2.98 D/mm) are close to the theoretical value (−2.7 D/mm). These data are referred to further in the study results described subsequently.

DETAILED DESCRIPTION OF PREFERRED FORMS

Referring to FIGS. 1-4, the contact lenses of the invention comprise a correction area or zone indicated at 1a in each of FIGS. 1-4 which has a focal length which will correct existing myopic vision of a wearer (the correction area or zone 1a has a negative focal power). The lenses comprise another area 1b which will simultaneously present a myopic defocused image to the wearer during both distance and near viewing, which is referred to herein as a treatment zone for convenience. That is, the treatment area is relatively less negative in focal power than the correction area 1a. It is possible that the treatment area may be up to 5 dioptres less negative in focal power than the correction area, more likely between 1 and 3 Dioptres less negative and typically about 2 Dioptres different. If the correction area for a particular subject with only mild myopia has a low negative focal power such as only 1 Dioptres negative for example, then it is possible that the treatment zone may have a neutral or low positive focal power.

Figure 1:
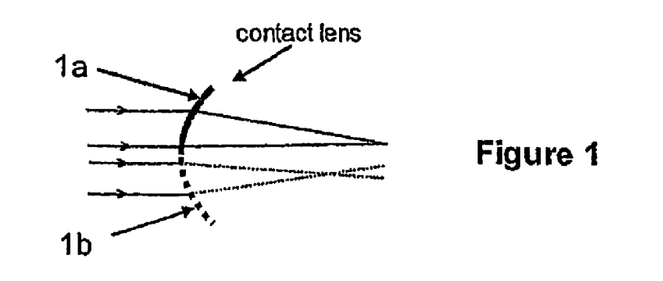
FIG. 1 schematically illustrates one form of a contact lens of the invention, from one side.
Figure 2:
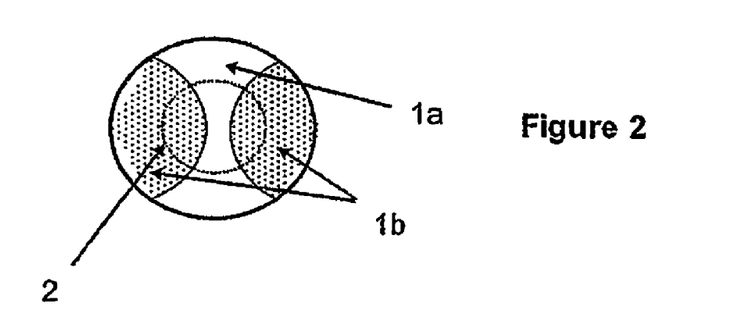
FIG. 2 is a front view of another form of a contact lens of the invention.
Figure 3:
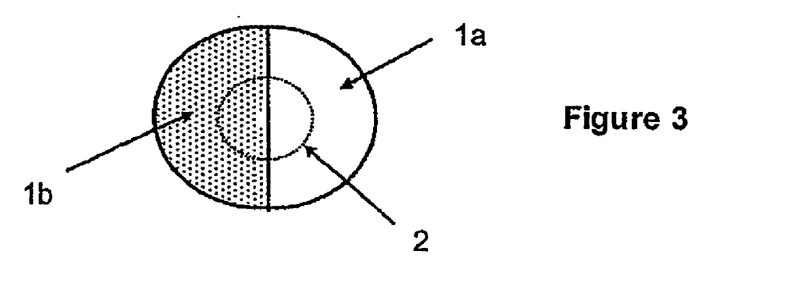
FIG. 3 is a front view of a further form of contact lens of the invention.
Figure 4:
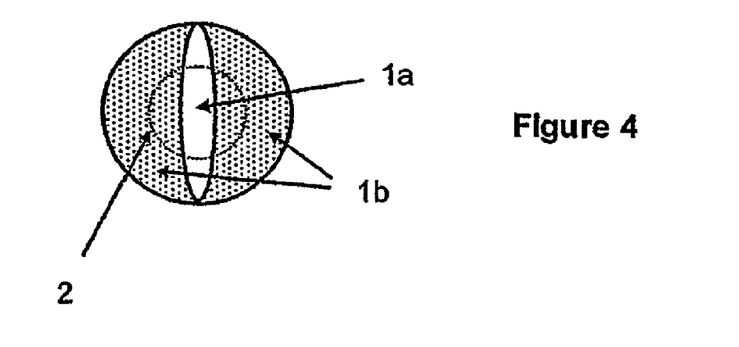
FIG. 4 is a front view of yet a further form of contact lens of the invention.

As shown in FIG. 2, the treatment zone may be composed of two separate part-circular shaped areas 1b as shown which impinge onto the area of the surface of the contact lens from either side (or above and below) while the balance of the lens comprises the correcting area or zone 1a. In FIGS. 2-4 the lens is shown in relation to the pupil margin of a typical wearer which is indicated at 2.

In FIG. 3 the treatment zone 1b which applies myopic defocus comprises one half of the lens while the correction zone 1a comprises the other half of the lens. In FIG. 4 the correction zone comprises a central ovaloid area of the lens while the treatment zone 1b comprises the balance of the surface area of the lens.

The invention is not limited to particular shapes of the areas of the correction and treatment zones on the lens or lenses and the treatment and correction zones may each make up any part of the area of the lens, provided that the net result is that the lens will simultaneously present to the wearer a clear retinal image and myopic defocus during both distance and near viewing. The lenses shown and the shapes of the correction and treatment areas are given by way of example only.

Figure 5A:
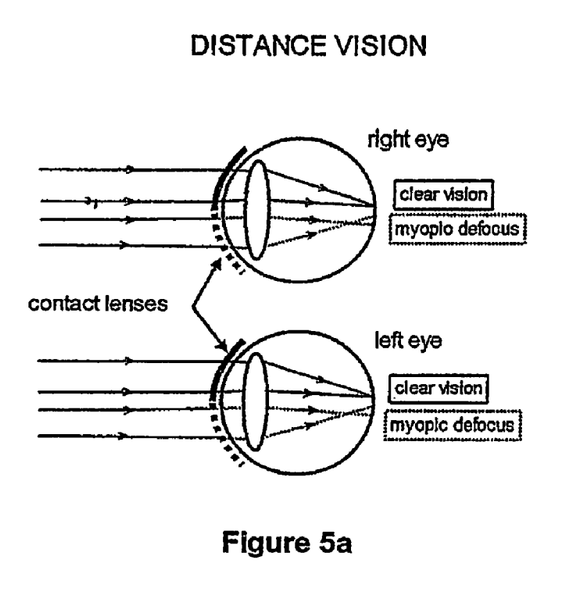
FIGS. 5a and 5b illustrate treatment of myopia progression by the method of the invention, as referred to further subsequently.
Figure 5B:
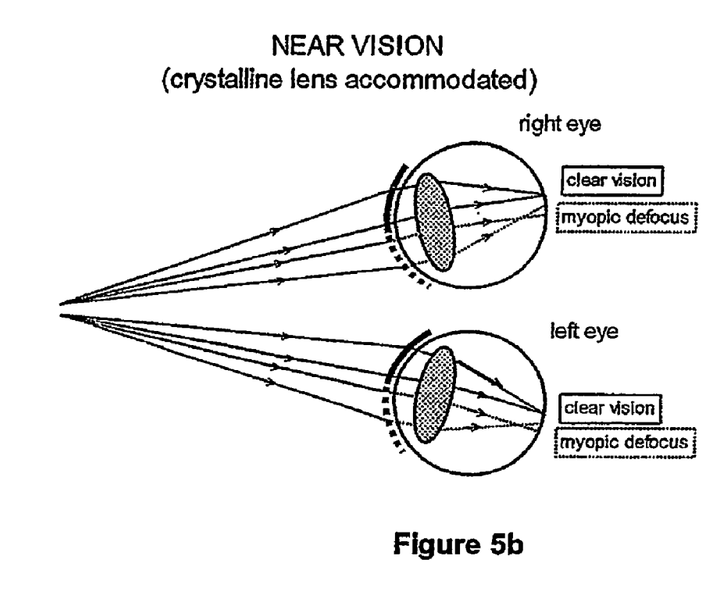

FIGS. 5a and 5b diagrammatically illustrate the effects of wearing of lenses of the invention and the method of the invention. During distance vision shown in FIG. 5a, accommodation is relaxed and images of distant objects are brought to focus on the retina via the correction zone of the lens, giving clear distance vision. In each case the correction zone of the each lens is indicated in solid and the treatment zone as a broken line. Simultaneously, light from the distant objects passes through the treatment zone of the lens and is brought to focus in front of the retina, causing myopic defocus on the retina. Although FIG. 5 shows (diagrammatically) the clear retinal image and the myopic defocus applied to different retinal locations, in reality the two images lie over the same retinal areas.

During near vision, shown in FIG. 5b, the convergence of the eyes necessary to maintain single binocular vision (and also the proximity of the reading target) cause the eyes to accommodate. In each eye, this accommodation brings the image transmitted through the correction zone into focus on the retina. This accommodation has the effect of maintaining a simultaneous myopic-defocused retinal image created by light passing through the treatment zone of the lenses.

The Effect on the Eye Over Time

The study described in detail below shows that when sustained myopic defocus is present in human eyes their rate of myopia progression is significantly slowed. In this study the dominant eyes of eighteen 11 year-old children with myopia between −1.00 and −3.00 D spherical equivalent were corrected for distance; the fellow eyes were un-corrected or corrected to keep the refractive imbalance≦2.00 D. Unexpectedly children accommodated to read with the distance-corrected eye, with the result that their under-corrected eye experienced myopic retinal defocus when viewing at both distance and near. Myopia progression was followed in both eyes with cycloplegic autorefraction and A-scan ultrasonography measures of vitreous chamber depth (VCD) made approximately every 8 months for between 8 and 30 months. Mixed effects modelling of the inter-eye differences in refraction and VCD showed that myopia progression in the under-corrected eyes was significantly slower than in the distance-corrected eyes (inter-eye difference in progression=0.37 D/yr (95% CI=0.57 to 0.18 D/yr, P=0.0005, n=13); difference in vitreous chamber elongation rate=0.13 mm/yr (95% CI=0.19 to 0.08 mm/yr, P=0.0001, n=13)). No inter-eye differences developed for lens thickness (P=0.383), anterior chamber depth (P=0.513) or corneal radius (P=0.537). The study shows that sustained myopic retinal defocus slows the progression of axial myopia in children:

Methods

Participants were 18 children (11 female, 7 male, mean age 11.6 years) with a variety of ethnic origins (10 East Asian, the remainder included Caucasian, South Asian (Indian) and Maori/Pacifica). Inclusion criteria were (i) ten to thirteen years of age (ii) no previous spectacle or contact lens wear (iii) both eyes having subjectively determined best-sphere refractions between −1.00 D to −3.00 D with astigmatism≦−1.00 DC and initial anisometropia≦1.00 D (iv) both eyes correctable to 6/6 Snellen acuity and (v) no binocular vision abnormality or ocular pathology. Stereopsis was assessed using the Wirt circles of the Stereotest (Stereo Optical Inc, Chicago, USA). Eye dominance was determined using a simple sighting test.

The dominant eyes of all children were corrected for distance because this is the most common procedure in monovision contact lens practice. The non-dominant eyes viewed through a piano lens unless the resultant refractive imbalance between the eyes exceeded 2.00 D, when the non-dominant eye was partially corrected to keep the imbalance equal to 2.00 D. As myopia progressed, the dominant eye was corrected to maintain 6/6 acuity while keeping the refractive imbalance no greater than 2.00 D. Participants were advised to build up to full-time wear as quickly as possible. Spectacle wear was either full-time (8 or more hours/day) or part-time.

Spherical equivalent refraction (SER), measured by cycloplegic autorefraction and vitreous chamber depth (VCD), measured by A-scan ultrasonography, were used to monitor myopia progression. Cycloplegia was induced with 1% Tropicamide (2 drops/eye, 5 minutes apart) after corneal anaesthesia with benoxinate: measures were made 30 minutes later. This protocol produces effective cycloplegia in children of this age. A portable autorefractor (Retinomax K-plus, Nikon Inc., Tokyo, Japan) was used to obtain 2 measures for each eye. Each measure was expressed in power-vector form, with M representing the spherical component and $J_0$ and $J_{45}$ the powers of the equivalent Jackson cross cylinders at axes 0° and 45°. The average M component was used as the measure of SER. Ocular component dimensions (anterior chamber depth, ACD, lens thickness LT, and axial length, AXL) were measured by A-scan ultrasonography (Ophthasonic a-scan/b-scan III, Teknar Inc, St Louis, USA). Vitreous chamber depth was computed as VCD=AXL−(ACD+LT) averaged form three measures for each eye. Measures were made on the day spectacles were dispensed (baseline) and at follow-up visits approximately 8 months apart for an average period of 18.7 months (range 8 to 30 months).

The accommodative status of the eyes when reading with the monovision prescription was determined by Cross-Nott dynamic streak retinoscopy. In this method, the working distance is varied in order to find the neutral retinoscopy reflex in each eye. At neutral, the plane of the retinoscope sight-hole coincides with the point in space conjugate with the retina.

Linear mixed-effects models were used to investigate the development of inter-eye differences over time. The model took account of the paired eyes, the repeated measures taken on the same eye and importantly, the different number of measurements made per subject. The models were fit in SAS (SAS Institute Inc. USA) using the procedure PROC MIXED and the Restricted Maximum Likelihood (REML) fitting algorithm.

Results

Monovision Spectacle Wear

After several months of adaptation to monovision, dynamic retinoscopy (see Methods) showed that all children (excluding 5 who dropped out of the study early) accommodated to read with the distance-corrected (dominant) eye rather than with the near-corrected eye. Consequently, the near-corrected eyes experienced myopic defocus at all levels of accommodation. Stereoacuity, which was 40 sec arc prior to recruitment, was typically reduced to between 40 and 80 sec arc with monovision, but returned to 40 sec arc with a conventional correction. Best-corrected acuity remained at baseline levels (typically 6/5) in all eyes.

Refractive Error Versus Time

Figures 6A, 6B:
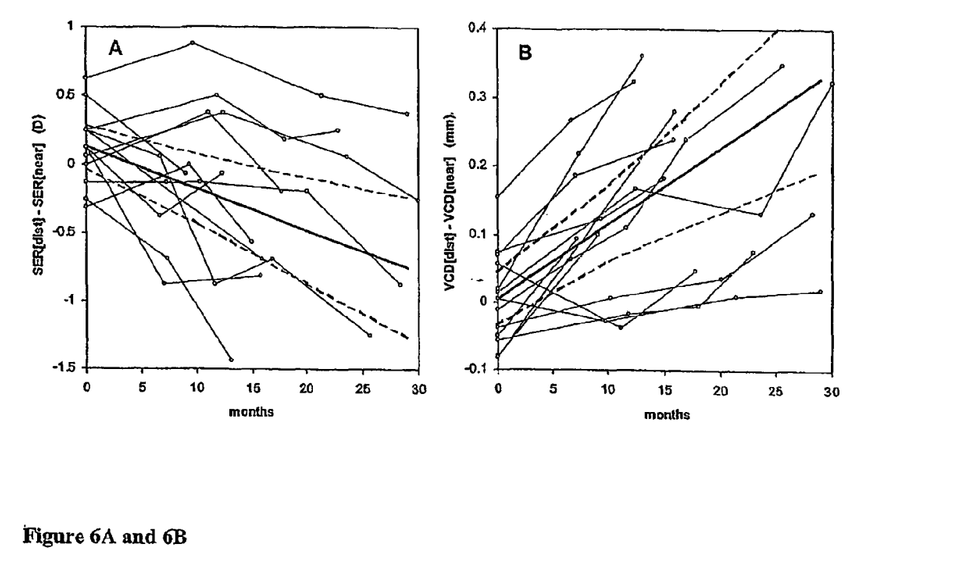
FIG. 6a shows the progressive difference that develops with time between the myopia in normally corrected eyes (SER[dist]) and myopia in eyes experiencing sustained myopic retinal defocus (SER[near]). For these children, eyes experiencing myopic defocus developed myopia at a rate 0.36 D/year less than the normally corrected eyes.
FIG. 6b shows that the vitreous chamber depth (VCD) of the eyes experiencing myopic defocus grew at a slower rate (difference=0.13 mm/yr) than the normally corrected eyes. These data are referred to further in the study results described subsequently.

The baseline SERs of distance-corrected eyes (−1.61±0.62 D (mean±SD) and near-corrected eyes (−1.69±0.67 D) were not different (P=0.383). Myopia progression during monovision wear, computed as (SER[afterMv]−SER[baseline])×12/(months of wear), gave a mean progression rate across participants of −0.72±0.32 D/yr in distance-corrected eyes and −0.32±0.30 D/yr in near-corrected eyes. FIG. 6A shows how the inter-eye difference in refraction (SER[dist]−SER[near]) developed over time for each of the participants and also the mixed-model estimate of the average population trajectory with 95% confidence intervals. The model estimated the average difference in myopia progression between the eyes as 0.36 D/yr (95% CI=0.54 to 0.19 D/yr, P=0.0015, n=13) with near-corrected eyes progressing more slowly than distance-corrected eyes. Similar analyses showed that no inter-eye differences developed for either $J_0$ (P=0.14) or $J_{45}$ (P=0.15). Analysis of the effect of part-time versus full-time wear of monovision suggested that the difference in progression rate (D/yr) between the two eyes was less in part-time wearers (P=0.04), but the difference in VCD elongation rate between the two eyes was not different for part-time and full-time wear (P=0.11).

Changes in Ocular Dimensions with Time

The mean baseline VCDs of the distance and near-corrected eyes were equal (17.02±0.63 mm) with ranges of 15.98 to 18.42 mm and 16.04 to 18.35 mm respectively. FIG. 6B shows the development of inter-eye difference in VCD between the distance- and near-corrected eyes (VCD[dist]−VCD[near]) over time for each of the participants. The mixed-model analysis showed the mean difference in vitreous chamber elongation rate equalled 0.13 mm/yr (95% CI=0.18 to 0.08 mm/yr, P=0.0003, n=13), with the near-corrected eyes elongating more slowly than the distance-corrected eyes. Similar analyses showed that axial length increased more slowly in near-corrected eyes than in distance-corrected eyes (mean difference=0.10 mm/yr (95% CI=0.19 to 0.02 mm/yr, P=0.016, n=13) but no inter-eye differences developed for lens thickness (P=0.253), anterior chamber depth (P=0.509) or corneal radius (P=0.451).

Correlation Between Changes in Refractive Error and Vitreous Chamber Depth

Figure 7A:
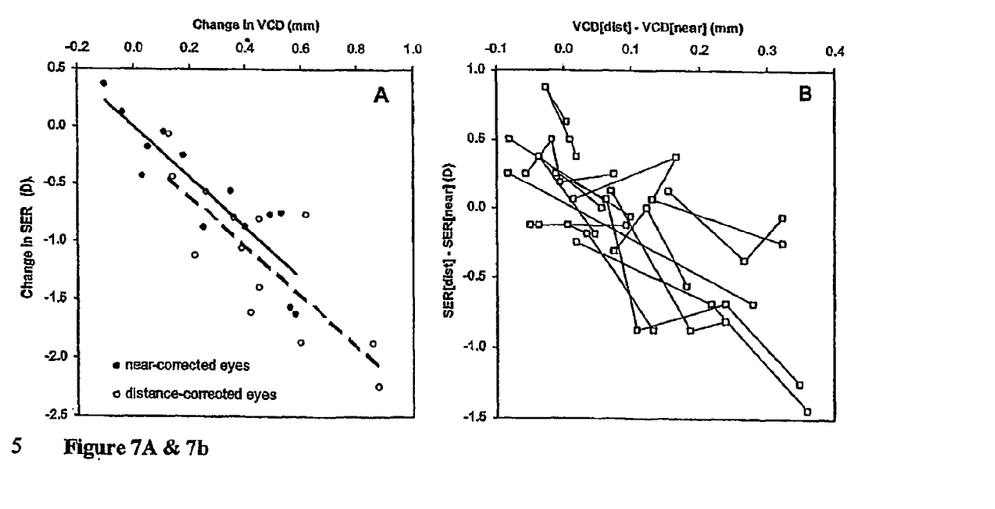

FIG. 7A shows the linear regression relationships between the change in SER during monovision wear (SER[afterMV]−SER[baseline]) and the change in VCD (VCD[afterMV]−VCD[baseline]) for all eyes. With refractive error as the dependent variable, the slopes of the relationships were similar (−2.16 D/mm, R=0.81, for distance-corrected eyes and −2.22 D/mm, R=0.88, for near-corrected eyes). Thus, although the progression rates were different in the two eyes, both rates correlated closely with increases in VCD. FIG. 7B illustrates the relationship between the difference in refractive error (SER[dist]−SER[near]) and the difference in VCD between the distance and near-corrected eyes (VCD[dist]−VCD[near]) at each visit for each participant. The slope of the relationship obtained by linear regression (not shown) equalled −2.98 D/mm (R=0.72).

The Effect of Eye Dominance

Figure 8:
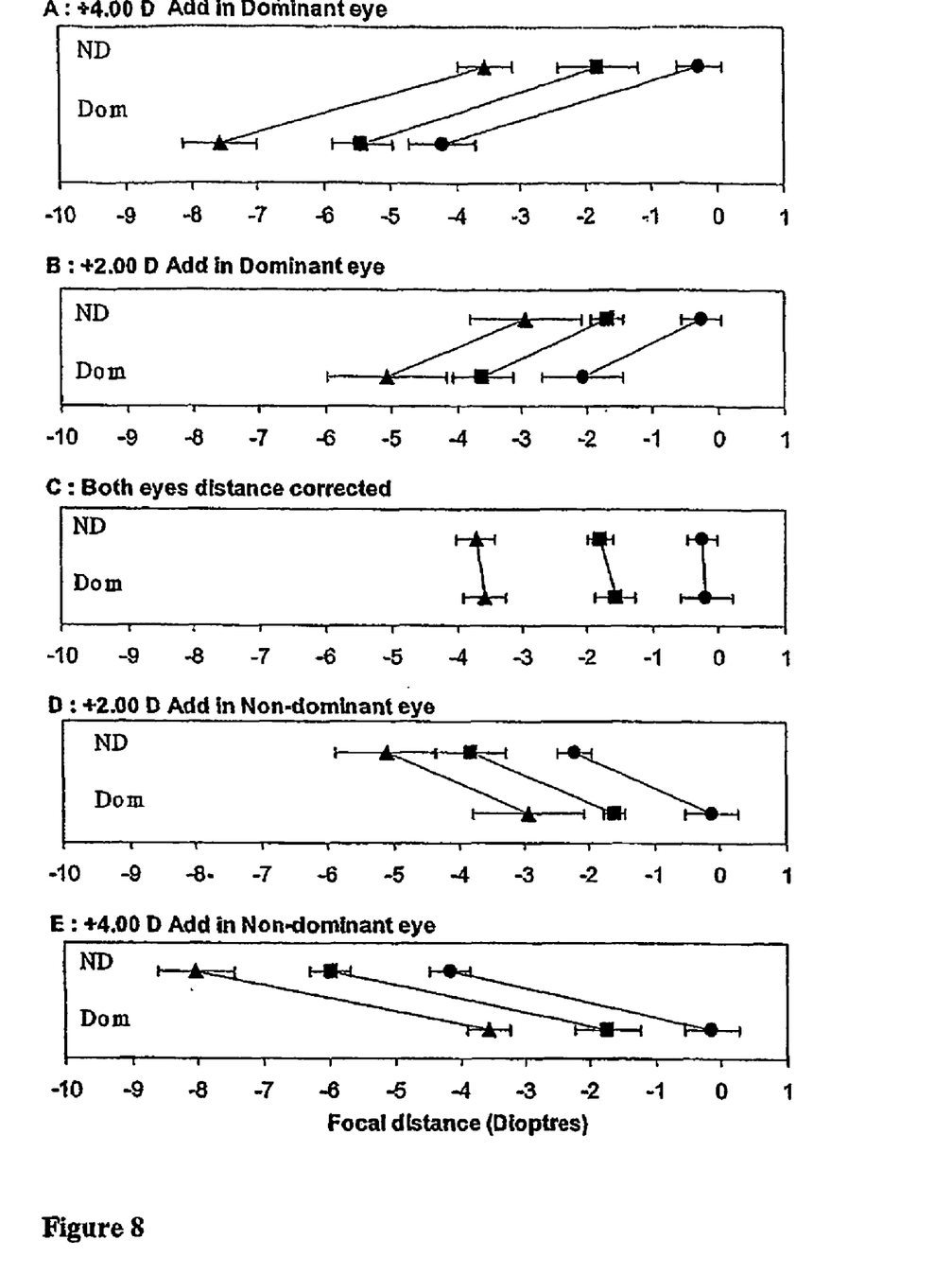
FIG. 8 shows that myopic defocus can readily be induced in either the dominant or the non-dominant eye when accommodating to read at near. These data and their relevance are referred to further in the study results described subsequently.

FIG. 8 shows that myopic defocus can readily be induced in either the dominant or the non-dominant eye when accommodating to read at near with a monovision correction. FIG. 8 shows the focal distance in dioptres (of the point in space conjugate with the retina) for each eye (ND: non-dominant, Dom: dominant) when reading at three different target distances (circles=target at 18 meters; squares=target at 50 cm; triangles=target at 25 cm) while wearing a CL monovision correction. Data are for 10 young subjects (mean age 23 yr), determined using a Shin Nippon autorefractor. [A & B] Non-dominant eye distance-corrected, with +4 add (A) or +2.00 D add (B) in Dominant eye. [C] Both eyes distance-corrected. [D & E] Dominant eye distance corrected, with +2 add (D) or +4.00 D add (E) in Non-dominant eye. Thus regardless of dominance, accommodation is exerted to bring the distance-corrected eye to focus on the reading target plane (0, −2 or −4 D) while inducing myopic defocus in the contra-lateral eye. These results imply that accommodation while reading is not driven primarily by defocus in either the dominant or non-dominant eye. Rather, accommodation is driven by the convergence of the eyes necessary to maintain single binocular vision (convergence accommodation) or by proximity cues (proximal accommodation), or both.

CONCLUSION

Unexpectedly, children wearing a monovision correction accommodated to read with the distance-corrected eye, causing the contra-lateral eye to experience sustained myopic defocus at both distance and near. Myopia progression and the associated abnormal axial growth of the eye were significantly reduced in all eyes experiencing sustained myopic defocus. Myopic defocus was induced in the contralateral eye whether the dominant or the non-dominant eye was corrected for distance. This indicates that accommodation is not driven by defocus in either the dominant or non-dominant eye, but rather by convergence of the eyes to maintain single binocular vision or by proximity cues. The results (surprisingly) indicate that sustained myopic retinal defocus acts as an anti-myopiagenic stimulus that counters abnormal axial elongation of the human eye. This conclusion is the opposite of that reached after bilateral under-correction of children with myopia by Chung et al (Vision Research, 42 (2002) 2555-2559).

The method and contact lenses of the invention in addition to correcting refractive error, apply continuous myopic retinal defocus in both eyes whether the wearer is viewing in the distance or at near. The effect of wearing the new contact lenses is that the myopic retinal defocus created by the lenses inhibits the abnormal axial elongation of the eyes that underlies myopia progression with the effect that over time, the progression of myopia slows, stops or reverses. The manifestations of the effect are (i) the progressive abnormal enlargement of the eye ceases, although depending on the age of the wearer, normal eye enlargement (growth) may still occur. (ii) the progressively increasing myopic refractive error, requiring progressively stronger minus power lenses to correct it, slows its rate of progression or ceases to progress.

The foregoing describes the invention including preferred forms thereof. Alternations and modifications as well be obvious to those skilled in the art are intended to be incorporated therein as defined in the accompanying claims.

The invention claimed is:

1. A method of slowing the progression of myopia in a person, comprising: applying to the eye or eyes of the person or prescribing for the person, a contact lens or lenses, each contact lens including a vision correction area comprising a focal power to correct the myopic vision of the person during distance viewing and to provide a clear retinal image during near viewing; and a myopic defocus area which comprises focal power less negative than the vision correction area focal power to simultaneously in use present a myopic defocused image to the person during both distance and near viewing, to thereby simultaneously present the eye or eyes of the person a clear retinal image and retinal myopic defocus during both distance and near viewing.

2. A method according to claim 1 comprising applying to the eye or eyes of the person or prescribing for the person, a contact lens or lenses the focal power of the myopic defocus area of which is up to 5 dioptres less negative than the focal power of the vision correction area.

3. A method according to claim 1 comprising applying to the eye or eyes of the person or prescribing for the person, a contact lens or lenses the focal power of the myopic defocus area of which is between about 1 and about 3 dioptres less negative than the focal power of the vision correction area.

4. A method according to claim 1 comprising applying to the eye or eyes of the person or prescribing for the person, a contact lens or lenses the focal power of the myopic defocus area of which is about 2 dioptres less negative than the focal power of the vision correction area.

5. A method according to claim 1 comprising applying to the eye or eyes of the person or prescribing for the person, a contact lens or lenses in which the myopic defocus area comprises two separate part-circular shaped areas which impinge onto the area of the surface of the contact lens from either side or from above and below and in which the balance of the lens comprises the vision correction area.

6. A method according to claim 1 comprising applying to the eye or eyes of the person or prescribing for the person, a contact lens or lenses in which the myopic defocus area comprises one half of the lens and the vision correction area comprises the other half of the lens.

7. A method according to claim 1 comprising applying to the eye or eyes of the person or prescribing for the person, a contact lens or lenses in which the vision correction area comprises a central ovaloid area of the lens and the myopic defocus area comprises the balance of the lens.

8. A contact lens, comprising: a vision correction area comprising a focal power to correct myopic vision of a person during distance viewing and to provide a clear retinal image during near viewing; and a myopic defocus area comprising a focal power less negative than the vision correction area focal power to simultaneously in use present a myopic defocused image to the person during both distance and near viewing, to thereby simultaneously present the eye or eyes of the person a clear retinal image and retinal myopic defocus during both distance and near viewing.

9. A contact lens according to claim 8, wherein the vision correction area comprises a negative focal power, and the myopic defocus area comprises a focal power less negative than the vision correction area focal power.

10. A contact lens according to claim 8 wherein the focal power of the myopic defocus area of the lens is up to 5 dioptres less negative than the focal power of the vision correction area.

11. A contact lens according to claim 8 wherein the focal power of the myopic defocus area of the lens is between about 1 and about 3 dioptres less negative than the focal power of the vision correction area.

12. A contact lens according to claim 8 wherein the focal power of the myopic defocus area the lens is about 2 dioptres less negative than the focal power of the vision correction area.

13. A contact lens according to claim 8 in which the myopic defocus area comprises two separate part-circular shaped areas which impinge onto the area of the surface of the contact lens from either side or from above and below and in which the balance of the lens comprises the vision correction area.

14. A contact lens according to claim 8 in which the myopic defocus area comprises one half of the lens and the vision correction area comprises the other half of the lens.

15. A contact lens according to claim 8 in which the vision correction zone comprises a central ovaloid area of the lens and the myopic defocus area comprises the balance of the lens.

16. A method of manufacturing a contact lens system or kit for treating or slowing the progression of myopia in a patient, comprising: providing two or more contact lenses which may be the same or different, at least one of which comprises a vision correction area for correcting in use the myopic vision of the patient and a myopic defocus area for simultaneously presenting in use a myopic defocused image to the patient.

17. A method according to claim 16, wherein the focal power of the myopic defocus area of which is up to 5 dioptres less negative than the focal power of the vision correction area.

18. A method according to claim 16, wherein the focal power of the myopic defocus area of which is between about 1 and about 3 dioptres less negative than the focal power of the vision correction area.

19. A method according to claim 16, wherein the focal power of the myopic defocus area of which is about 2 dioptres less negative than the focal power of the vision correction area.

* * * * *